US010032613B2

(12) United States Patent
Van Riper et al.

(10) Patent No.: US 10,032,613 B2
(45) Date of Patent: Jul. 24, 2018

(54) NON-PARAMETRIC METHODS FOR MASS SPECTROMIC RELATIVE QUANTIFICATION AND ANALYTE DIFFERENTIAL ABUNDANCE DETECTION

(71) Applicant: Regents of the University of Minnesota, Minneapolis, MN (US)

(72) Inventors: Susan Van Riper, Minneapolis, MN (US); John V. Carlis, Minneapolis, MN (US); Timothy J. Griffin, St. Anthony, MN (US); Ebbing de Jong, Minneapolis, MN (US); LeeAnn Higgins, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 132 days.

(21) Appl. No.: 14/090,961

(22) Filed: Nov. 26, 2013

(65) Prior Publication Data

US 2014/0200821 A1 Jul. 17, 2014

Related U.S. Application Data

(60) Provisional application No. 61/731,302, filed on Nov. 29, 2012.

(51) Int. Cl.
*G01N 33/48* (2006.01)
*H01J 49/00* (2006.01)
*G06G 7/58* (2006.01)

(52) U.S. Cl.
CPC ................................ *H01J 49/0036* (2013.01)

(58) Field of Classification Search
CPC .......... G06F 19/18; G06F 19/20; G06F 19/22; G01N 33/66; G01N 33/582
See application file for complete search history.

(56) References Cited

U.S. PATENT DOCUMENTS

| | | | |
|---|---|---|---|
| 6,334,099 | B1 | 12/2001 | Grace et al. |
| 6,835,927 | B2 | 12/2004 | Becker et al. |
| 6,906,320 | B2 | 6/2005 | Sachs et al. |
| 7,087,896 | B2 | 8/2006 | Becker et al. |
| 7,626,162 | B2 | 12/2009 | Hashiba et al. |

OTHER PUBLICATIONS

Bantscheff, Marcus, "Mass spectrtrometry-based chemoproteomic approaches", J Chemical Proteomics: Methods and Protocols, Methods in Molecular Biology, vol. 803—Chapter 1, (2012), 3-13.

Bland, J, Martin, et al., "Statistical methods for assessing agreement between two methods of clinical measurement", The Lancet, (Feb. 8, 1986), 307-310.

Bondarenko, Pavel V., et al., "Identification and relative quantitation of protein mixtures by enzymatic digestion followed by capillary reversed-phase liquid chromatography-tandem mass-spectrometry", Anal. Chem, 74, (2002), 4741-4749.

Cravatt, Benjamin F., et al., "The biological impact of mass-spectrometry-based proteomics", Nature, vol. 450/13, (2007), 991-1000.

Griffin, Timothy J., et al., "Complementary profiling of gene expression at the transcriptome and proteome levels in *Saccharomyces cerevisiae*", Molecular & Cellular Proteomics, 1,4, (2002), 323-333.

Jung, Stephanie, et al., "Microchip electrospray: cone-jet stability analysis for water-acetonitrile and water-methanol mobile phases", Journal of Chromatography A, 1218, (2011), 1611-1619.

Karpievitch, Yuliya, et al., "Normalization of peak intensities in bottom-up MS-based proteomics using singular value decompsition", Bioinformatics, vol. 25, No. 19, (2009), 2573-2580.

Kultima, Kim, "Development and evaluation of normalization methods for label-free quantification of endogenous peptides", Molecular & Cellular Proteomics, (2009), 2285-2295.

Oberg, Ann L., et al., "Statistical design of quantitative mass spectrometry-based proteomic experiments", Journal of Proteome Research, vol. 8, No. 5, (2009), 2144-2156.

Prakash, Amol, et al,, "From Signal Maps for Mass Spectrometry-based Comparative Proteomics", Molecular & Cellular Proteomics, 5.3, (2006), 423-432.

Ramanathan, Ragu, et al., "Response normalized liquid chromatograhy nanospray ionization mass spectrometry", J Am Soc Mass Spectrom, 18, (2007), 1891-1899.

Rudnick, et al., "Peformance metrics for liquid-chromatography—tandem mass-spectrometry systems in proteomics analysis", Molecular & Cellular Proteomics, 9.2, (Oct. 16, 2009), 225-241.

(Continued)

*Primary Examiner* — Eric S Dejong
(74) *Attorney, Agent, or Firm* — Schwegman Lundberg & Woessner, P.A.

(57) ABSTRACT

A method of normalizing data can comprise globally normalizing at least a first and second data distribution by normalizing the proximal compositional proportionality of the abundance of the analyte using proximity-based intensity normalization. In an example, the proximity-based intensity normalization comprising using the following formula:

$$\frac{i_{jx}}{\sum_{j=1}^{n_x} i_{jx}} \Big/ \frac{i_{jy}}{\sum_{j=1}^{n_y} i_{jy}}$$

wherein:

$i_{jx}$ is the intensity of ion j in the first distribution x,
$i_{jy}$ is the intensity of ion j in the second distribution y,
$n_x$ is the number of surrogate ions in distribution x, and
$n_y$ is the number of surrogate ions in distribution y.

14 Claims, 10 Drawing Sheets

(56) References Cited

OTHER PUBLICATIONS

Voyksner, Robert D., et al., "Investigating the use of an octupole ion guide for ion storage and high-pass mass filtering to improve the quantitative performance of elctrospray on trap mass spectrometry", Rapid Communications in Mass Spectrometry, 13, (1999), 1427-1437.

Reduction in CV

| | Regression | Loess | Quantile | Reference | Median Scale | PIN |
|---|---|---|---|---|---|---|
| Instrument Variability | 0.22 | 0.22 | 0.21 | 0.22 | 0.21 | 0.49 |
| Sample Variability | 0.10 | 0.11 | 0.10 | 0.10 | 0.10 | 0.40 |
| Serial Dilution | 0.24 | 0.30 | 0.22 | 0.23 | 0.27 | 0.59 |
| CPTAC C vs E | -0.23 | -0.03 | -0.22 | 0.01 | -0.24 | 0.18 |

FIG. 3C

Reduction in PEV

| | Regression | Loess | Quantile | Reference | Median Scale | PIN |
|---|---|---|---|---|---|---|
| Instrument Variability | 0.15 | 0.15 | 0.16 | 0.14 | 0.14 | 0.76 |
| Sample Variability | 0.11 | 0.11 | 0.12 | 0.11 | 0.11 | 0.71 |
| Serial Dilution | 0.40 | 0.43 | 0.37 | 0.37 | 0.37 | 0.77 |
| CPTAC C vs E | 0.11 | 0.08 | 0.13 | 0.04 | 0.11 | 0.61 |

FIG. 3D

NON-PARAMETRIC METHODS FOR MASS SPECTROMIC RELATIVE QUANTIFICATION AND ANALYTE DIFFERENTIAL ABUNDANCE DETECTION

CROSS-REFERENCE TO RELATED APPLICATIONS

This application claims the benefit under 35 U.S.C. § 119(e) of U.S. Provisional Application Ser. No. 61/731,302 filed on Nov. 29, 2012, which is hereby incorporated by reference in its entirety.

STATEMENT REGARDING FEDERALLY SPONSORED RESEARCH OR DEVELOPMENT

This invention was made with Government support under agency grant number DE017734 from the National Institutes of Health. The Government has certain rights in the invention.

BACKGROUND

Mass spectrometry can help researchers analyze chemical and biological samples (Cravatt B F, 2007; Bantscheff M, 2012). Mass spectrometry techniques can allow for measurement of the mass and concentration of atoms and molecules. Analysis of samples can provide insight into the molecular makeup of samples obtained from one or more populations, and can help facilitate studies aimed at investigating a biological activity. In particular, quantitative mass spectrometry can provide relatively specific and sensitive data that can allow comparison of biological samples taken at various time points. Such quantitation can allow for comparison of biological variation, and can foster understanding of the molecular machinery of cellular activity and disease progression.

Intensity-based label free relative quantification using high performance liquid chromatography coupled with electrospray ionization and tandem mass spectrometry (HPLC-ESI-MS/MS) can help researchers reveal biological variation by employing large scale comparative experiments in which two or more populations are compared (Oberg A L, 2009). In the context of label free relative quantification, a population can be comprised of biological and/or technical replicates from a biological state in common, e.g., healthy or diseased.

These large scale comparative experiments require normalization in order to allow for meaningful comparison of data from different experiments. Sample measurements can be biased by effects such as the efficiency of sample extraction or systematic effects due to characteristics of the chromatographic quantification itself. Accordingly, normalization attempts to compensate for such effects.

Present normalization methods can include the regression analysis model which can be used to efficiently calibrate sample variance. It can be used to estimate a scaling factor between two populations, to account for variance in coverage.

Another analysis model can include the LOESS (“LOcal regrESSion”) normalization method, which is a form of regression modeling method. The LOESS method can combine more than one regression model into meta-model. The LOESS method can take into account intensity dependent effects, and in some cases can partially correct for background effects. A variant of this model can take into account local effects.

The quantile regression method is another method that can complement the classical linear regression analysis, by allowing a user to make a more subtle inference of the effect of an explanatory variable on a dependent variable. The median scale method can be used for data normalization by adjusting the scale of the data, such as by setting the median of differences to 0. In this method of normalization, all of the various datasets are adjusted, not just the median quantile. As such, a potential drawback to the scale normalization method is that the method does not consider any region or intensity dependent effects.

Known normalization methods can be adequate for use with current label-free relative quantification paradigms for detecting biological variation within HPLC-ESI-MS/MS workflows in the absence of extraneous variability. However, extraneous variability is inherent in HPLC-ESI-MS/MS workflows. Known global normalization methods can mitigate systematic bias somewhat, but when complex variability is present, known methods do not perform well. In fact, known global normalization methods can work well to mitigate systemic bias, but can also increase variability in data rather than reduce it.

Becker et al., U.S. Pat. Nos. 7,087,896 and 6,835,927, are both directed toward obtaining relative quantitative information regarding components of chemical or biological samples that can be obtained from mass spectra, such as by normalizing the spectra to yield peak intensity values that accurately reflect concentrations of the responsible species.

Hashiba et al., U.S. Pat. No. 7,626,162, is directed toward relative quantitative analysis of a liquid mixture of two samples, such as biological samples, labeled with stable isotopes using a liquid chromatography-tandem mass spectrometry system.

Sachs et al., U.S. Pat. No. 6,906,320, is directed toward mass spectrometry data analysis techniques that can be employed to selectively indentify analytes differing in abundance between different sample sets.

Grace et al., U.S. Pat. No. 6,334,099, is directed toward methods for normalization of experimental data with experiment-to-experiment variability.

The following references, to the extent that they provide exemplary procedural or other details supplementary to those set forth herein, are specifically incorporated herein by reference.

Bantscheff. “Mass spectrometry-based chemoproteomic approaches.” Methods Mol Biol. 803:3-13, 2012.

Bland, Altman. “Statistical methods for assessing agreement between two methods of clinical measurement.” Lancet. 1:307-10, 1986.

Bondarenko, Chelius, Shaler. “Identification and relative quantitation of protein mixtures by enzymatic digestion followed by capillary reversed-phase liquid chromatography-tandem mass spectrometry.” Anal Chem. 74:4741-9, 2002.

Cravatt, Simon, Yates. “The biological impact of mass-spectrometry-based proteomics.” Nature. 13:991-1000, 2007.

Griffin, Gyfi, Ideker, Rist, Eng, Hood, Aebersold. “Complementary profiling of gene expression at the transcriptome and proteome levels in Saccharomyces cerevisiae.” Mol Cell Proteomics. 1:323-33, 2002.

Jung, Effelsberg, Tallarek. “Microchip electrospray: cone-jet stability analysis for water-acetonitrile and water-methanol mobile phases.” J Chromatogr A. 1218:1611-9, 2011.

Karpievitch, Taverner, Adkins, Callister, Anderson, Smith, Dabney. “Normalization of peak intensities in bottom-up MS-based proteomics using singular value decomposition." Bioinformatics. 25:2573-80, 2009.

Kultima, Nilsson, Scholz, Rossbach, Fäith, Andrén. "Development and evaluation of normalization methods for label-free relative quantification of endogenous peptides." Mol Cell Proteomics. 8:2285-95, 2009.

Oberg, Vitek. "Statistical design of quantitative mass spectrometry-based proteomic experiments." J Proteome Res. 8:2144-56, 2009.

Ramanathan, Zhong, Blumendrantz, Chowdhury Alton. "Response normalized liquid chromatography nanospray ionization mass spectrometry." J Am Soc Mass Spectom. 18:1891-9, 2007.

Rudnick, Clauser, Kilpatrick, Tchekhovskoi, Neta, Blonder, Billheimer, Blackman, Bunk, Cardasis, Ham, Jaffe, Kinsinger, Mesri, Neuber, Schilling, Tabb, Tegeler, Vega-Montoto, Variyath, Wang, Wand, Whiteaker, Zimmerman, Carr, Fisher, Gibson, Paulovich, Regnier, Robriquez, Spiegelman, Tempst, Leibler, Stein. "Performance metrics for liquid chromatography-tandem mass spectrometry systems in proteomics analyses." Mol Cell Proteomics. 9:225-41, 2010.

Voyksner, Lee. "Investigating the use of an octupole ion guide for ion storage and high-pass mass filtering to improve the quantitative performance of electrospray ion trap mass spectrometry." Rapid Commun Mass Spectrom. 13:1427-37, 1999.

OVERVIEW

The present inventors have recognized, among other things, that a problem to be solved can include inadequate mitigation of extraneous sample variability using surrogate ion intensities normalized by global methods, which can lead to poor repeatability and reproducibility. The present subject matter can provide a solution to this problem by improving measurement repeatability and reproducibility, such as by measuring compositional proportionality rather than simple relative abundance. This can be achieved by a new method disclosed herein, which normalizes each analyte's abundance (as measured by its surrogate ion's intensity) by computing its proximal compositional proportionality.

Within large scale comparative experiment workflows, biological samples can be prepared, possibly fractionated, and loaded onto a high-performance liquid chromatography (HPLC) column. An analyte can be ionized via electrospray ionization (ESI). Resulting ions can be subjected to tandem mass spectrometry (MS/MS) which can detect and record ion signal intensity and fragment intensity. Although mass spectrometers are not intrinsically quantitative, an ion's signal intensity loosely correlates to the source analyte's physical (absolute) abundance in the sample measured by, for example, its molar amount (Voyksner R D, 1999; Bondarenko P V, 2002). Thus, measuring an ion's intensity can be a surrogate for measuring an analyte's abundance.

Researchers commonly assert that an analyte is differentially abundant if the fold-change between populations (relative abundance as measured by its surrogate ion intensity ratio across HPLC-ESI-MS/MS runs) satisfies some criterion (Griffin T J, 2002). Although the criterion should be set based on sample and instrument characteristics, the de-facto fold-change threshold can be a factor of two, which can translate to a relative abundance ≥2.0 or ≤0.5 between populations. A problem exists with such a criterion because a fold change less than two would signify no change, although the analyte can still be differentially abundant.

Additional problems exist with current methods because label free relative quantification HPLC-ESI-MS/MS workflows can suffer from poor repeatability and reproducibility which can interfere with detecting biological variation. As used herein, "repeatability" means the ability to produce the same result in a repeated measurement of the same sample using the same system and operator (Bland J M, 1986). On the other hand, as used herein, "reproducibility" means the ability to produce the same result in a repeated experiment where the analytical technique remains the same, but the operator, instrumentation, time, or location is changed.

Despite globally normalizing HPLC-ESI-MS/MS chromatographic data, researchers report that poor repeatability and reproducibility still occurs. This poor repeatability and reproducibility can lead to results containing excessive false positive and false negative data concerning differentially abundant analytes. A false positive analyte can eventually be discarded via hypothesis driven experiments, but at the cost of valuable researcher time. A false negative analyte can be more misleading than a false positive, because a researcher might never look at the rejected analyte and thus miss possible insight, leading the researcher to draw an incorrect conclusion. The present inventive subject matter posits that the (simple ratio) relative abundance fold change paradigm is ill-suited to discover differentially abundant analytes in label free relative quantification for HPLC-ESI-MS/MS experiments.

In response, the present inventive subject matter proposes a new paradigm for label free relative quantification via HPLC-ESI-MS/MS, referred to herein as "the proportionality paradigm." Under the proportionality paradigm, instead of computing relative abundance, i.e., the simple ratio of two surrogate ion intensities, the new paradigm computes an analyte's ratio of compositional proportions between two populations. The present inventive subject matter further proposes a new normalization method, referred to herein as "proximity-based intensity normalization" (PIN) which can mitigate extraneous variability by applying the proportionality paradigm locally. PIN can provide the solution for mitigating both systemic bias and complex variability.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 1A illustrates the anticipated abundance of analytes 1-3 in samples A, B, and C. FIG. 1B illustrates the anticipated fold change in samples A vs. B, A vs. C and B vs. C. FIG. 1C illustrates the actual (absolute) abundance of analytes 1-3 in samples A, B, and C. FIG. 1D illustrates the relative abundance fold change in samples A vs. B, A vs. C and B vs. C. FIG. 1E illustrates the proportions of analytes 1-3 in samples A, B, and C. FIG. IF illustrates the relative proportions fold change in samples A vs. B, A vs. C and B vs. C.

FIG. 2A illustrates extracted peptide signal chromatograms where a trough is observed in the second replicate's chromatogram in the same time frame as the observed electrospray instability. FIG. 2B illustrates normalization producing nearly identical extracted chromatograms. FIG. 2C illustrates the application of a global normalization method such as median scale method, which fails to mitigate the complex variability.

FIG. 3A illustrates the coefficient of variation (CV). FIG. 3B illustrates the pooled estimate of variance (PEV). FIG. 3C illustrates reduction in CV. FIG. 3D illustrates reduction in PEV.

FIG. 4A illustrates un-normalized measurements. FIG. 4B illustrates measurements normalized by spiked-in standard. FIG. 4C illustrates measurements normalized by PIN method. FIG. 4D illustrates measurements normalized by PIN scaled by loading amount.

FIG. 5A illustrates un-normalized extracted chromatograms. FIG. 5B illustrates chromatograms normalized by median scale method. FIG. 5C illustrates chromatograms normalized by the PIN method.

DETAILED DESCRIPTION

Figure 1:
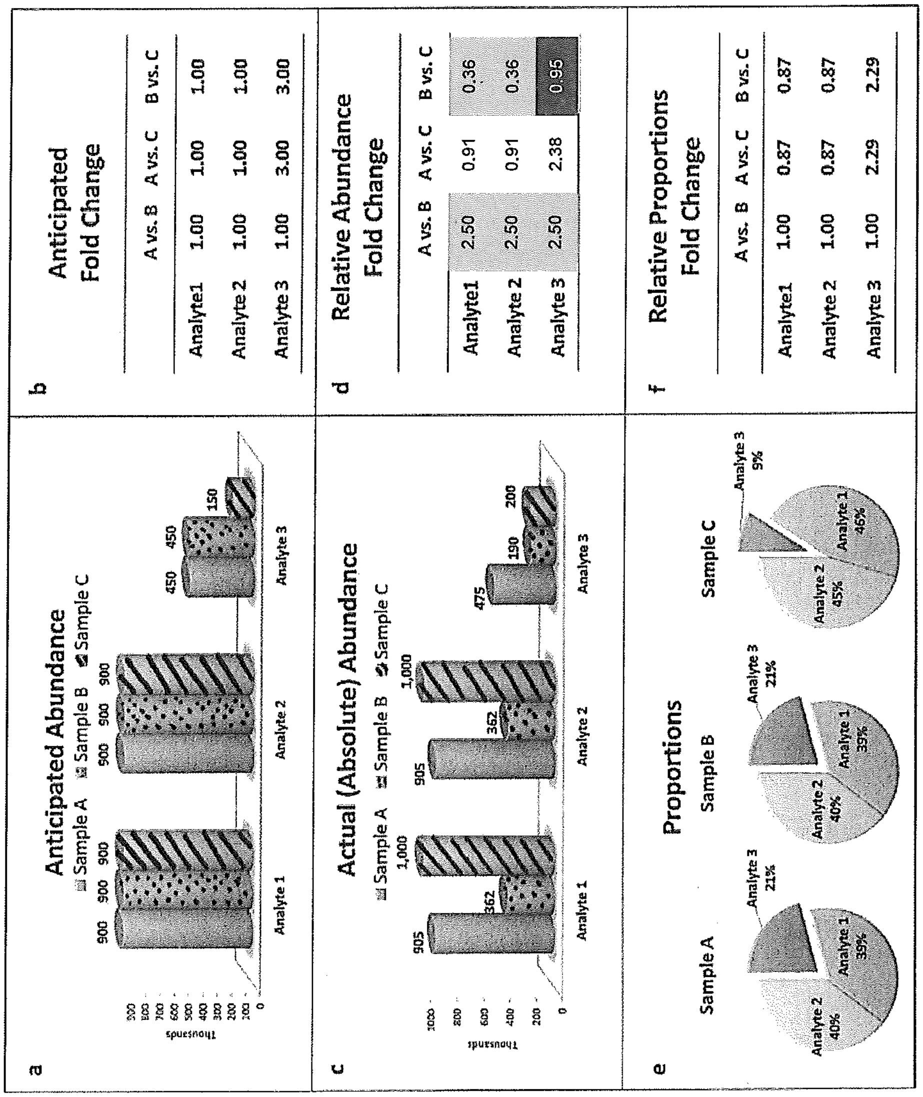
FIG. 1 illustrates the proportionality paradigm for label free relative quantification via HPLC-ESI-MS/MS.

Variance in HPLC-ESI-MS/MS chromatographic data can result from true biological variation. Biological variation can include, but is not limited to, differential expression of a polymer, such as DNA, RNA, PNA, protein, peptide, carbohydrate, or modified forms thereof. As such, an analyte, as discussed herein, can include, but is not limited to, a peptide, metabolite, or pharmaceutical compound.

Variance in data can result from extraneous variability comprised of systematic bias (sample variability and instrument variability), or complex variability. Sample variability can stem from inconsistent sample preparation, including, but not limited to, incomplete enzymatic digestion, differences in sample storage condition, pipetting errors, etc. Sample variability can be global, e.g., each analyte in a sample, or in the case of a pipetting error each analyte in an aliquot can be similarly affected and can result in systematic bias.

Instrument variability can stem from a physical change in the mass spectrometry hardware or environment, including, but not limited to, HPLC column degradation, calibration drift, etc. Instrument variability can also be global in nature, since each ion's intensity in a run can be similarly affected and can result in systematic bias.

Complex variability can stem from signal distortion due to transient stochastic events that occur during an HPLC-ESI-MS/MS run, such as by variability in ESI performance due to mobile phase composition or flow rate fluctuations (Jung S, 2011; Ramanathan R, 2007). Complex variability can be deemed complex because each event will affect only a narrow temporal window of an HPLC-ESI-MS/MS run, the temporal window duration can vary, or one or more windows can overlap.

Normalization can attempt to make two or more distributions similar. In the context of a HPLC-ESI-MS/MS workflow, the normalization attempt can be an adjustment in data such that similar samples will produce similar chromatographic intensity distributions such that the chromatographic distribution in each sample is representative of true biological variation.

The known global normalization method called the proportionality paradigm can mitigate systematic bias, but the proportionality paradigm can fail from a problem frequent in global normalization methods. Known global normalization methods frequently do not capture and mitigate temporally localized, complex variability (Karpievitch Y V, 2009). The failure to capture and mitigate complex variability is particularly problematic because complex variability during an HPLC-ESI-MS/MS is almost inevitable, even when following a strict operating protocol.

Various Notes and Examples

The proportionality paradigm disclosed herein can address the problem of failing to capture and mitigate complex variability. The proportionality paradigm, as applied locally can be embodied in a new algorithm named proximity-based intensity normalization (PIN). PIN can provide the advantage of revealing label-free relative quantification of biological variation missed with current methods.

A normalization technique of HPLC-ESI-MS/MS workflows can incorporate a method that relies on a global scaling function. The global scaling function can be modeled using one or more signals within an HPLC-ESI-MS/MS run, e.g., median scale, quantile, ranking, and least squares fitting using linear or polynomial regression (Kultima K, 2009). The general formula for computing fold changes incorporating normalization is:

$$\frac{i_{jx}}{s_{jx}} \bigg/ \frac{i_{jy}}{s_{iy}},$$

where $i_{jx}$=intensity of ion j in run x, $i_{jy}$=intensity of ion j in run y, and $s_{jx}$ and $s_{jy}$ are scaling factors computed by a global function for runs x and y respectively. By defining a new global scaling function as $s_{jx}=\Sigma_{j=1}^{n_x} i_{jx}$, i.e., where $n_x$ is the number of surrogate ions in run x, then the global normalization formula becomes $$\frac{i_{jx}}{\sum_{j=1}^{n_x} i_{jx}} \bigg/ \frac{i_{jy}}{\sum_{j=1}^{n_y} i_{jy}}$$

which can be the formula for the relative proportion under the PIN proportionality paradigm. Thus, the PIN proportionality paradigm can be an improved method of both reporting fold changes (relative proportions) and providing a global normalization method.

General Methods

A biological sample was prepared and loaded onto an HPLC column according to methods known in the art.

Analytes including, but not limited to, peptides and metabolites, were then ionized via ESI, and resulting ions were subjected to MS/MS which detects and records ion signal intensity and fragment intensities. The PIN normalization method was implemented to mitigate extraneous variability. As illustrated in the following examples, the PIN method can provide for computation of an analyte's ratio of compositional proportions between two populations rather than relative abundance.

To implement PIN, a new Java-based framework named RIPPER was developed. The RIPPER program can rip out of mzXML files only chromatographic peaks associated with true peptide signals. Within RIPPER, PIN can normalize an analyte's surrogate ion intensity by first constructing the ion intensity's temporal neighborhood and then computing the relative proportion within the neighborhood.

PIN was evaluated in relation to common normalization methods using spectral data from four HPLC-ESI-MS/MS experiments performed on complex peptide mixtures. The resulting chromatograms did not require retention time alignment as manual inspection revealed minimal retention time drift (<40 seconds) between runs. The following examples illustrate the ability of the PIN method to mitigate extraneous variability while applying the proportionality paradigm locally. Examples illustrating the ability of PIN to mitigate systemic bias and complex variability that can be introduced by instrumentation, sample handling, and differences in loading amounts also follow. The following examples also illustrate the ability of PIN to retain true biological variability.

PIN results were compared to results from other global normalization methods using the reduction in median standard deviation coefficient of variance (CV) or pooled estimate of variance (PEV) as quality metrics. Numerous normalization methods were analyzed, but only the five best performing methods are reported as determined by CV and PEV reduction. In comparing the results of the experiments, PIN's superior mitigation of systematic bias and complex variability along with retaining true biological variability can be demonstrated.

The inventive subject matter will be further described by the following non-limiting examples where results are reported below from the application of PIN to HPLC-ESI-MS/MS data derived from complex peptide mixtures. The results show that PIN dominates current global normalization by mitigating extraneous variability while retaining biological variation.

Example 1

Known Global Normalization Methods Fail to Mitigate Complex Variability

Figure 2:
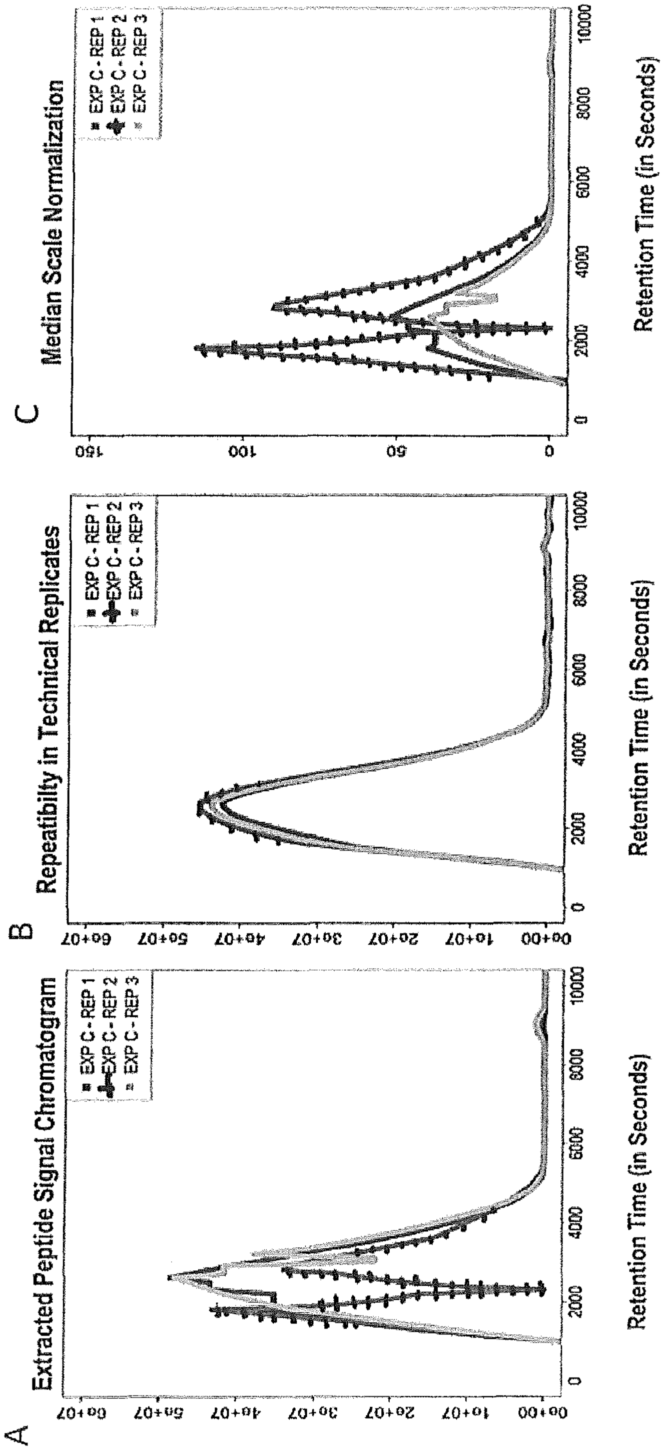
FIG. 2 illustrates chromatograms taken from three replicate analyses generated from the Clinical Proteomic Tumor Analysis Consortium (CPTAC).

The following example is particularly illustrative of the drawbacks of using known global normalization methods. The National Cancer Institute established the Clinical Proteomic Tumor Analysis Consortium (CPTAC) to enable inter-laboratory comparison of proteomic studies, particularly in the context of discovery cancer biomarkers. In the $6^{th}$ study, the CPTAC produced a community reference data set and standard operating procedures for preparing a yeast proteome digest containing 48 spiked in proteins (UPS1 standard from Sigma Aldrich). Using the CPTAC dataset generated by instrument aliased LTQ-Orbitrap@65P, irregularities were found in one of three replicate analyses due to electro spray instability (Rudnick P A, 2010). The dataset, having a distinctive saw tooth pattern can be a textbook example of complex variability. While modestly diminished peptide identification performance was reported for the second replicate analysis, it is possible that the complex variability also diminished intensity based peptide quantification performance. Extracted peptide signal chromatograms were reviewed for the CPTAC data set and a trough in the second replicate's chromatogram was observed in the same time frame as the observed electro spray instability (FIG. 2A). Ideally, normalization would produce nearly identical extracted chromatograms (XCs) (FIG. 2B).

However, the application of a global normalization method such as median scale method failed to mitigate the complex variability (FIG. 2C). In addition, the global normalization method had the unintended consequence of adversely affecting regions where no complex variability exists. The adverse effect is illustrated by the two regions of the XC having more extraneous variability than before normalization.

Complex variability can similarly affect measured ion intensities within close proximity (temporal window or neighborhood). Based on this observation, it can be reasoned that at the neighborhood level, complex variability becomes systematic bias. However, applying a proximal normalization method in the form of the proportionality paradigm locally can mitigate both systematic bias and complex variability.

Example 2

PIN Mitigates Variability While Retaining True Biological Variability

Relative abundance and fold change was used to determine if an analyte is differentially abundant. Sample A and sample B are examples of two aliquots from the same parent sample. As such, without a pipetting error, one would expect the anticipated amount of analyte in each sample to be equal (FIG. 1A). In sample C, a pipetting error can cause the sample to contain roughly three times less analyte by volume (FIG. 1A and B). In this example, the analyte's relative abundance using its surrogate ion intensity is the ratio:

$$\frac{i_{jx}}{i_{jy}}$$

where $i_{jx}$=intensity of ion j in sample x and $i_{jy}$=intensity of ion j in sample y, and differential abundance is a fold change of two or more. By this definition the constituent analytes appear differentially abundant between Samples A and B. The relative abundance is approximately 2.5 (FIG. 1D). However, based on sample composition, the constituent analytes do not appear differentially abundant between Samples A and B because both samples were pipetted from the same parent sample. Whether the constituent analytes are differentially abundant between samples A and B is up for interpretation, and is therefore ambiguous. A more suitable analysis can focus on whether the constituent analytes are differentially proportionate between the two samples. To address this question, relative proportions can be measured across samples. An analyte's relative proportion using its surrogate ion intensity is $$\frac{i_{jx}}{\sum_{j=1}^{n_x} i_{jx}} \Big/ \frac{i_{jy}}{\sum_{j=1}^{n_y} i_{jy}}$$

where $i_{jx}$=intensity of ion j in run x, $i_{jy}$=intensity of ion j in run y, and n is the number of ions in respective runs, as discussed above. That is, the analyte's relative proportion can be measured by first computing the surrogate ions' proportional intensity within a run and then comparing proportional intensities across samples. Computing the analyte's compositional proportion and then the fold change of the analyte answers the question of whether the constituent analytes are differentially proportionate between the two samples correctly with three "no" answers.

Analyte abundances can be known, such as in Sample C. Constituent analyte abundances were compared using known methods. When constitutent analyte abundances were compared between Sample C and parent samples A and B, whether the constituent analytes are differentially abundant depends on whether Sample C is compared against Sample A or Sample B. False negatives (FIG. 1D, box shaded in dark grey) and false positives (FIG. 1D, boxes shaded in light grey) were both found, along with correct results (FIG. 1D, boxes shaded). When the PIN method was used, correct results were given, e.g., analyte 3 was shown to be differentially abundant, but analyte 1 and analyte 2 were not (FIG. 1F). When the PIN method was used, whether correct results were achieved did not depend upon whether Sample C was compared to Sample A or Sample B. Therefore, unlike known methods of relative abundance paradigms which fail, the PIN method can correctly detect analytes with true biological variation.

Merely characterizing fold changes between two unreplicated samples can oversimplify the detection of biological variation via HPLC-ESI-MS/MS. Inherent extraneous variability can interfere with the precise measurement of ion intensities thereby making resulting fold changes untrustworthy. Researchers therefore turn to statistical tests such as t-test and ANOVA to determine which fold changes are significantly different. However, these tests require a minimum of three replicates and are sensitive to variance in measured intensities (Oberg A L, 2009).

To investigate the impact of variance, Sample A and Sample C were each analyzed three times via HPLC-ESI-MS/MS. In the first analysis, the fold change of Analyte 3 between Sample A and Sample C exceeded the fold change threshold, but was not statistically significant due to large variance (FIG. 1). In the second analysis, with low variance, the fold change of Analyte 3 can be statistically significant, but the fold change does not meet the specified well accepted fold-change criterion (FIG. 1). Therefore, minimizing variance, i.e., mitigating extraneous variability, can allow detection of biological variation not by detecting the fold change of an analyte and determining whether that fold change exceeds some numerical threshold, but from determining whether that fold change is statistically different.

Example 3

Instrument Variability

Figure 3A:
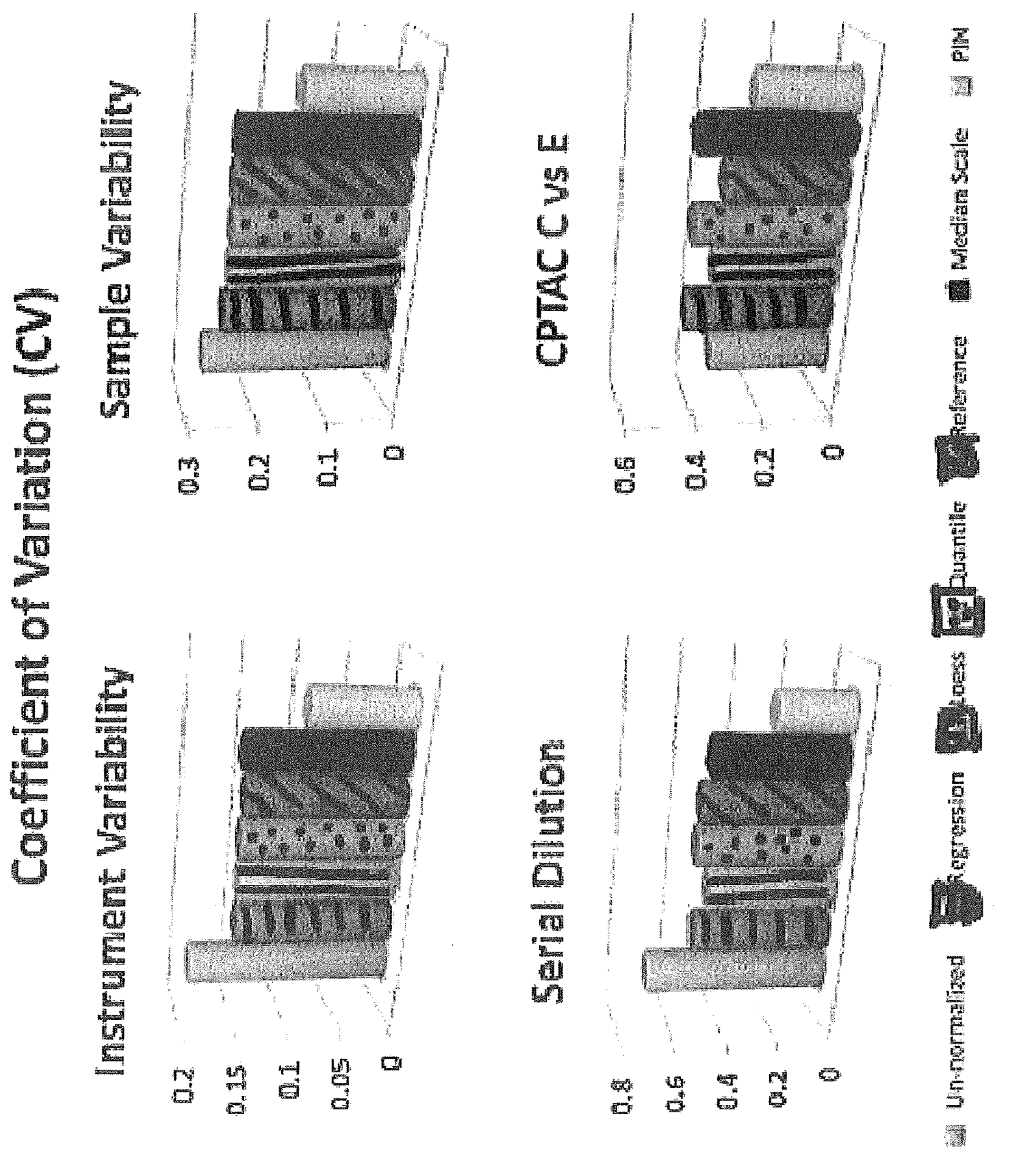
FIGS. 3A-3B illustrates the results of generating three replicates by analysis of a single aliquot of salivary endogenous peptides using an auto-sampler and HPLC-MS/MS. Results are shown for instrument variability, sample variability, serial dilution and the CPTAC C vs. E data set, when comparing un-normalized measurements, regression method, loess method, quantile method, reference method, median scale method or PIN.

The ability of PIN to reduce variability resulting from instrumentation was assessed by generating three replicates by analyzing a single aliquot of salivary endogenous peptides. Each single aliquot was analyzed three consecutive times using an auto-sampler and HPLC-MS/MS. PIN outperformed the five best known normalization methods by reducing CV and PEV compared to known methods. Known methods reduced CV by about 15% on average, while PIN reduced CV by 49% (FIG. 3C). PIN reduced PEV by 76% compared to the reduction by known methods, which reduced PEV by 15% (FIG. 3D).

Example 4

Sample Variability

The ability of PIN to reduce the variability resulting from sample handling was also assessed. The same methods were followed as when assessing instrument variability except three aliquots of salivary endogenous peptides were analyzed in parallel, each aliquot being analyzed using an auto-sampler and HPLC-MS/MS. PIN results were compared to known methods. Again, PIN results outperformed known normalization methods. PIN reduced CV by 40% compared to an average of about 10% when using known methods (FIG. 3C). PIN reduced PEV by 71% compared to an average of about 11% when using known methods (FIG. 3D).

Example 5

Serial Dilution

Figure 5A:
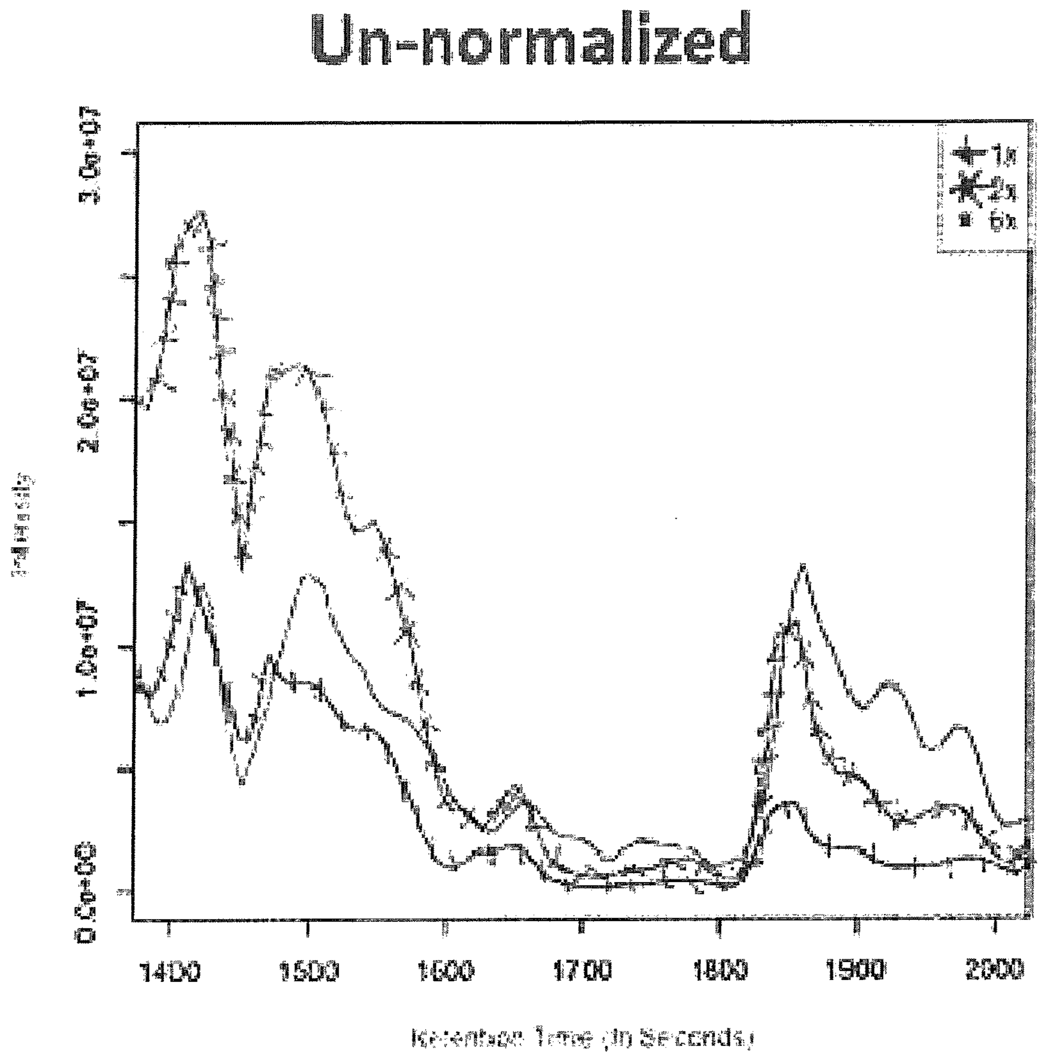
FIGS. 5A-5C illustrates the results of serial dilution experiments using a complex mixture of salivary endogenous peptides and bradykinin as a spiked in standard.
Figure 5B:
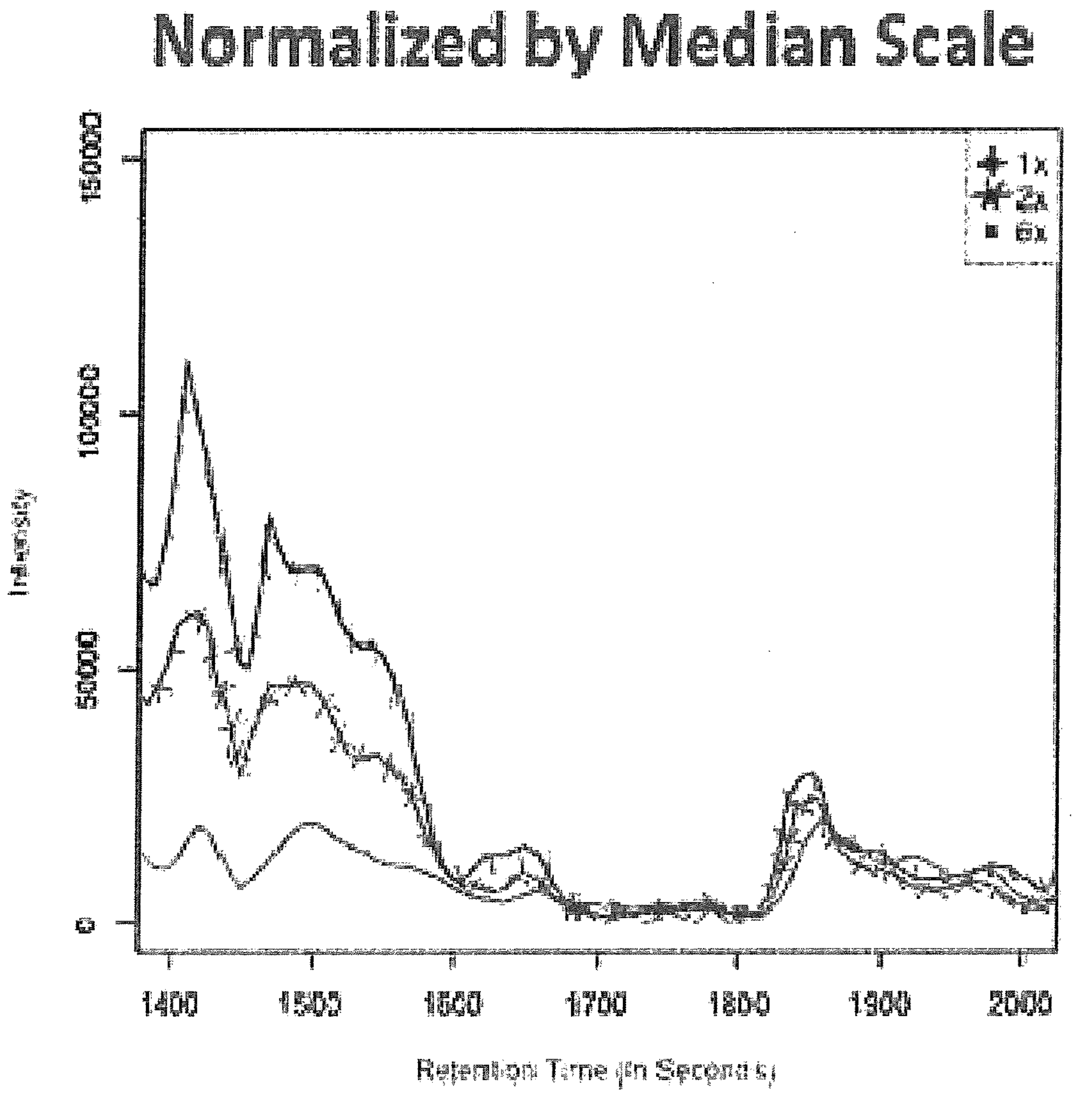
Figure 5C:
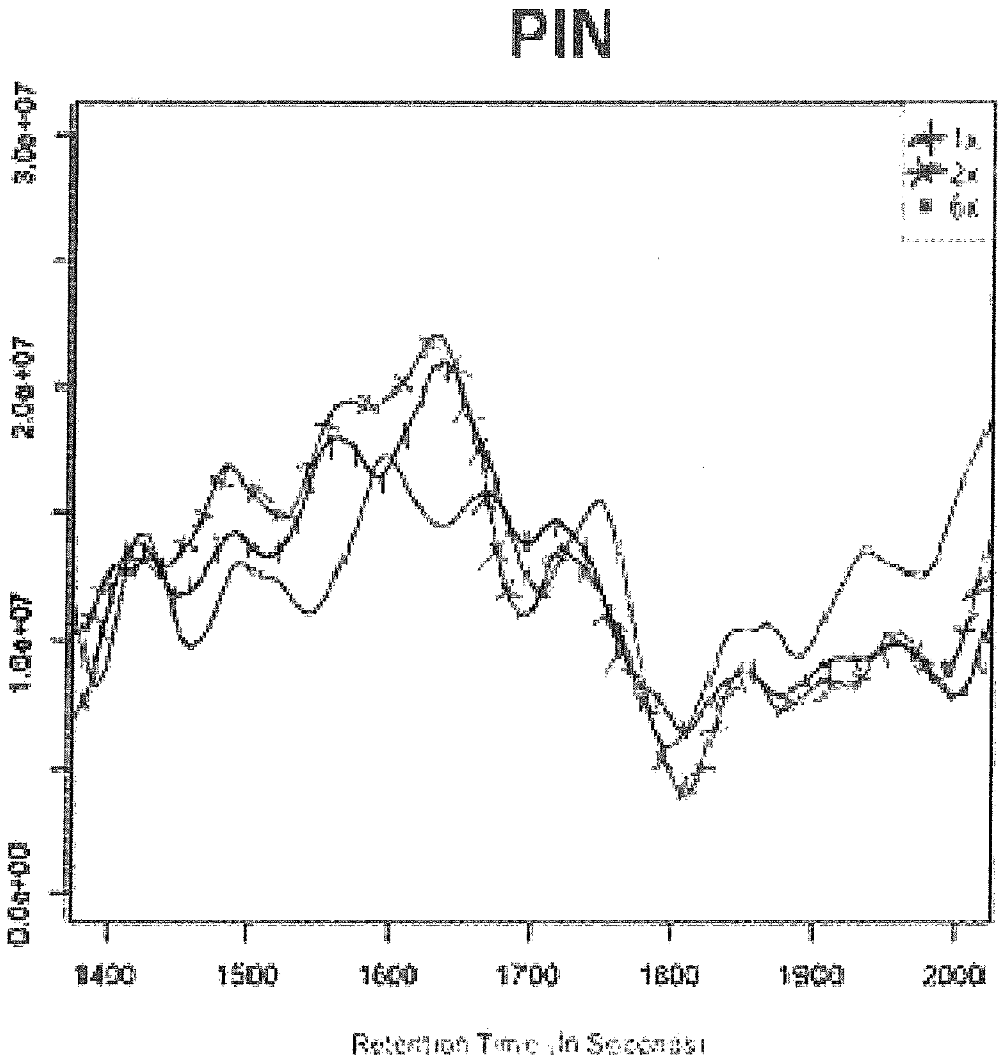

The ability of PIN to reduce the variability resulting from loading amount was also assessed. Serial dilution experiments were performed using a complex mixture of salivary endogenous peptides and bradykinin as a spiked in standard. Six aliquots of the complex mixture were prepared by combining increasing amounts (0.5, 1.0, 1.5, 2.0, 2.5, and 3.0 μg) of salivary endogenous peptides with an equal amount of bradykinin and analyzed them via HPLC-ESI-MS/MS. The 0.5, 1.0, and 3.0 μg extracted chromatograms demonstrated systemic bias (time period of 1600-2000 seconds) as well as complex variability (time period 1400-1600 seconds) (FIG. 5A). Known median scale normalization methods perform well to mitigate systematic bias (FIG. 5B). However, known median scale normalization methods do not minimize complex variability well (chromatograms diverge with intensity inversion—0.5 run's intensity>3.0 run's intensity). PIN, on the other hand, performs well to mitigate both systematic bias and complex variability (FIG. 5C).

PIN results were compared to known normalization methods. PIN reduced CV by 59% whereas known normalization methods reduced CV by about an average of 38% (FIG. 3C). PIN reduced PEV by 78% whereas known normalization methods reduced PEV by only about 26% (FIG. 3D).

Figure 4:
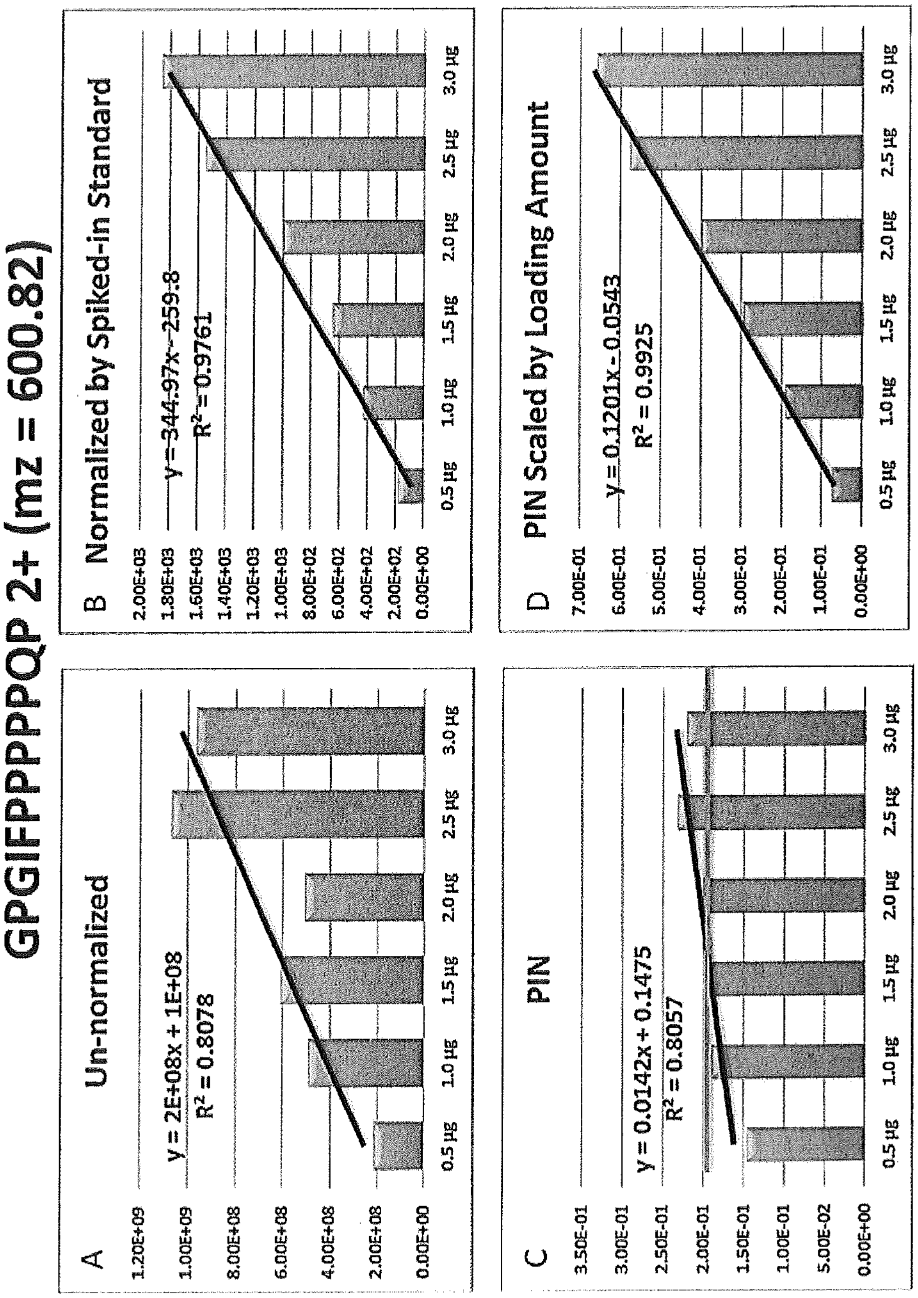
FIG. 4 illustrates the square of the correlation between the measurement values and predicted measurement values taken in a serial dilution experiment.

Typically in a serial dilution experiment, the standard metric employed is $R^2$, with the goal of $R^2$=1.0. When un-normalized intensity for a single example peptide in each of the 6 runs was plotted, $R^2$=0.80 (FIG. 4A). When the intensity is normalized using bradykinin's measured intensity, $R^2$ improves to 0.98 (FIG. 4B). Reporting CV and PEV reduction in a serial dilution experiment differs from reporting reduction values in instrument and sample handling experiments because if analyzed aliquots come from the same parent sample, their constituent analytes are not differentially abundant. Therefore, rather than achieving an $R^2$=1.0, the goal should be to achieve a slope=0.0. When normalization was performed with PIN, a slope of 0.01 was achieved (FIG. 4C). Because the approximate loading amounts were known, the actual amount of an analyte loaded onto the HPLC column can be estimated by scaling normalized intensities by the run loading amount. Scaling the PIN results by the loading amount achieves $R^2=0.995$. (FIG. 4D).

Example 6

Biological Variation

Figure 3B:
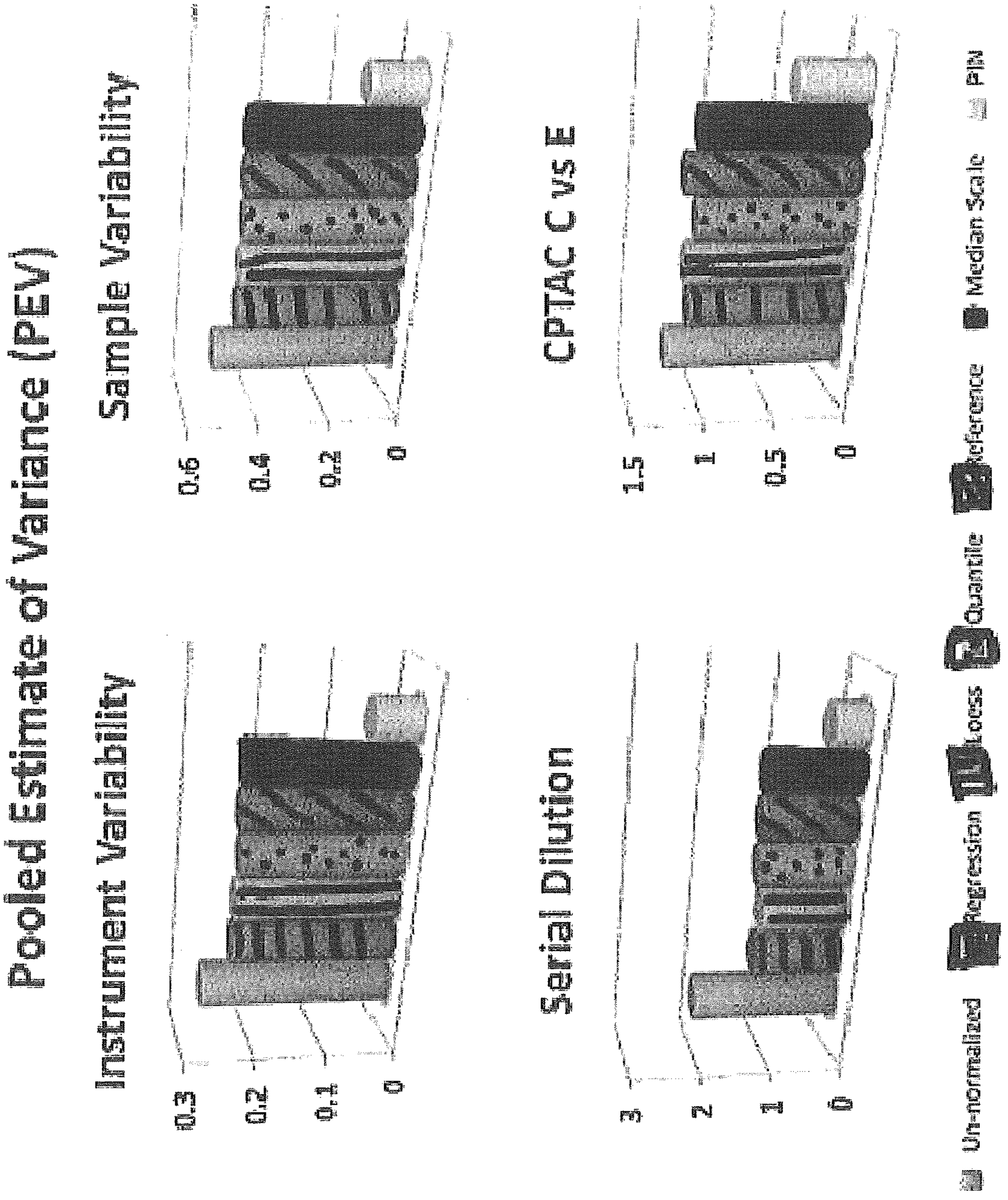

Overfitting can occur when a statistical model describes random error or noise instead of the underlying relationship. To evaluate overfitting, experiments were performed to assess PIN's ability to detect biological variation using data from the CPTAC Study 6 data set for instrument LTQ-XL-OrbitrapP@65. CPTAC Study 6 evaluated samples of yeast with Sigma UPS1 spiked in at 5 different levels (FIG. 4; A through D), each level three-fold greater than the previous level. Each sample was then analyzed three times by HPLC-ESI-MS/MS. Spike in levels C vs. E and D vs. E, having a 9 and 3-fold change in Sigma UPS1 proteins respectively were used. Prior to identifying proteins and peptides, CV and PEV metrics were employed to measure reduction in peptide signal variability. Using the C vs. E data set, PIN again outperformed known normalization methods (FIG. 3). PIN reduced PEV by 18% while common normalization methods, on average, increased PEV by about 5% (FIG. 3C). PIN reduced CV by 61% compared to an increase of about 14% when known normalization methods were used (FIG. 3D).

To identify the peptide signals, the data analysis program SEQUEST followed by the proteome identification software Scaffold was used. As a result, 46 out of the 48 UPS1 and yeast proteins were identified, with a false discovery rate (FDR) of <1%. An Oracle 11 g database was used to join Scaffold reported peptide and protein identifications with PIN results using charge and m/z matching criteria. A one sided student's t-test ($\alpha=0.95$, $p<0.01$) was employed to generate a list of proteins and peptides with significant fold changes between samples. Using the C vs. E dataset, statistically significant fold changes were detected for 39 of 46 UPS1 proteins (131 of 353 UPS1 peptides) prior to normalization and 40 of 46 UPS1 proteins (134 of 353 UPS1 peptides) after normalization with PIN. Furthermore, 218 of 619 yeast proteins (352 of 2924 yeast peptides) were detected, but only (185 of 2924 yeast peptides) after normalization with PIN. Thus, PIN did not overfit the C vs. E dataset. In fact, it allowed detection of statistically significant differences in approximately the same number of UPS1 proteins and peptides (true positives) while decreasing the number of yeast proteins and peptides (false positives).

Each of these non-limiting examples can stand on its own, or can be combined in various permutations or combinations with one or more of the other examples.

To better illustrate methods disclosed herein, a non-limiting list of Embodiments of the disclosed subject matter is provided here:

EMBODIMENT 1 can include subject matter (such as an apparatus, a device, a method, or one or more means for performing acts), such as can include a method of normalizing data, the method comprising globally normalizing at least a first and second data distribution by normalizing the proximal compositional proportionality of the abundance of the analyte using proximity-based intensity normalization.

EMBODIMENT 2 can include, or can optionally be combined with the subject matter of EMBODIMENT 1, to optionally include the proximity-based intensity normalization involving the following formula:

$$\frac{i_{jx}}{\sum_{j=1}^{n_x} i_{jx}} \Big/ \frac{i_{jy}}{\sum_{j=1}^{n_y} i_{jy}}$$

wherein:

$i_{jx}$ is the intensity of ion j in the first distribution x, $i_{jy}$ is the intensity of ion j in the second distribution y, $n_x$ is the number of surrogate ions in distribution x, and $n_y$ is the number of surrogate ions in distribution y.

EMBODIMENT 3 can include, or can optionally be combined with the subject matter of one or any combination of EMBODIMENTS 1 and 2, to optionally include at least one data distribution being obtained from a chromatographic method coupled with mass spectrometry.

EMBODIMENT 4 can include, or can optionally be combined with the subject matter of EMBODIMENT 3, to optionally include the chromatographic method comprising high performance liquid chromatography.

EMBODIMENT 5 can include, or can optionally be combined with the subject matter of one or any combination of EMBODIMENTS 3 and 4, to optionally include the mass spectrometry comprising electrospray ionization.

EMBODIMENT 6 can include, or can optionally be combined with the subject matter of one or any combination of EMBODIMENTS 3-5, to optionally include the mass spectrometry comprising tandem mass spectrometry.

EMBODIMENT 7 can include, or can optionally be combined with the subject matter of one or any combination of EMBODIMENTS 3-6, to optionally include at least one data distribution being obtained from high performance liquid chromatography coupled with electrospray ionization and tandem mass spectrometry.

EMBODIMENT 8 can include, or can optionally be combined with the subject matter of one or any combination of EMBODIMENTS 1-7, to optionally include the method improving the ability to produce the same result in a repeated measurement of the same sample using the same system and operator.

EMBODIMENT 9 can include, or can optionally be combined with the subject matter of one or any combination of EMBODIMENTS 1-8, to optionally include the method improving the ability to produce the same result in a repeated experiment where the analytical technique remains the same.

EMBODIMENT 10 can include, or can optionally be combined with the subject matter of one or any combination of EMBODIMENTS 1-9, to optionally include at least one data distribution being obtained from measurement of an ion's intensity as a surrogate for measuring an analyte's abundance.

EMBODIMENT 11 can include, or can optionally be combined with the subject matter of one or any combination of EMBODIMENTS 1-10, to optionally include at least one data point within at least one data distribution being indicative of an analyte within a sample.

EMBODIMENT 12 can include, or can optionally be combined with the subject matter of EMBODIMENT 11, to optionally include the sample being a biological sample.

EMBODIMENT 13 can include, or can optionally be combined with the subject matter of EMBODIMENT 12, to optionally include the biological sample being analyzed for quantitation of a polymer.

EMBODIMENT 14 can include, or can optionally be combined with the subject matter of EMBODIMENT 13, to optionally include the polymer comprising deoxyribonucleic acid (DNA).

EMBODIMENT 15 can include, or can optionally be combined with the subject matter of one or any combination of EMBODIMENTS 13 and 14, to optionally include the polymer comprising ribonucleic acid (RNA).

EMBODIMENT 16 can include, or can optionally be combined with the subject matter of one or any combination of EMBODIMENTS 13-16, to optionally include the polymer comprising peptide nucleic acid (PNA).

EMBODIMENT 17 can include, or can optionally be combined with the subject matter of one or any combination of EMBODIMENTS 13-16, to optionally include the polymer comprising one or more proteins.

EMBODIMENT 18 can include, or can optionally be combined with the subject matter of one or any combination of EMBODIMENTS 13-17, to optionally include the polymer comprising one or more peptides.

EMBODIMENT 19 can include, or can optionally be combined with the subject matter of one or any combination of EMBODIMENTS 13-18, to optionally include the polymer comprising one or more carbohydrates.

EMBODIMENT 20 can include, or can optionally be combined with the subject matter of one or any combination of EMBODIMENTS 13-19, to optionally include the polymer comprising a modified form of deoxyribonucleic acid (DNA).

EMBODIMENT 21 can include, or can optionally be combined with the subject matter of one or any combination of EMBODIMENTS 13-20, to optionally include the polymer comprising a modified form of ribonucleic acid (RNA).

EMBODIMENT 22 can include, or can optionally be combined with the subject matter of one or any combination of EMBODIMENTS 13-21, to optionally include the polymer comprising a modified form of peptide nucleic acid (PNA).

EMBODIMENT 23 can include, or can optionally be combined with the subject matter of one or any combination of EMBODIMENTS 13-22, to optionally include the polymer comprising a modified form of one or more proteins.

EMBODIMENT 24 can include, or can optionally be combined with the subject matter of one or any combination of EMBODIMENTS 13-23, to optionally include the polymer comprising a modified form of one or more peptides.

EMBODIMENT 25 can include, or can optionally be combined with the subject matter of one or any combination of EMBODIMENTS 13-24, to optionally include the polymer comprising a modified form of one or more carbohydrates EMBODIMENT 26 can include, or can optionally be combined with the subject matter of one or any combination of EMBODIMENTS 12-25, to optionally include the biological sample being analyzed for quantitation of a pharmaceutical compound.

EMBODIMENT 27 can include, or can optionally be combined with the subject matter of one or any combination of EMBODIMENTS 12-26, to optionally include the biological sample comprising blood.

EMBODIMENT 28 can include, or can optionally be combined with the subject matter of one or any combination of EMBODIMENTS 12-27, to optionally include the biological sample comprising urine.

EMBODIMENT 29 can include, or can optionally be combined with the subject matter of one or any combination of EMBODIMENTS 1-28, to optionally include the method computing the proportional ratio of an analyte between the two data distributions.

EMBODIMENT 30 can include, or can optionally be combined with the subject matter of one or any combination of EMBODIMENTS 1-29, to optionally include the method reducing a median standard deviation coefficient of variance quality metric.

EMBODIMENT 31 can include, or can optionally be combined with the subject matter of one or any combination of EMBODIMENTS 1-29, to optionally include the method minimizing the median standard deviation coefficient of variance quality metric.

EMBODIMENT 32 can include, or can optionally be combined with the subject matter of one or any combination of EMBODIMENTS 1-31, to optionally include the method reducing a median standard deviation pooled estimate of variance quality metric.

EMBODIMENT 33 can include, or can optionally be combined with the subject matter of one or any combination of EMBODIMENTS 1-32, to optionally include the method minimizing the median standard deviation pooled estimate of variance quality metric.

EMBODIMENT 34 can include, or can optionally be combined with the subject matter of one or any combination of EMBODIMENTS 1-33, to optionally include the method mitigating systemic bias.

EMBODIMENT 35 can include, or can optionally be combined with the subject matter of one or any combination of EMBODIMENTS 1-34, to optionally include the method mitigating complex variability.

EMBODIMENT 36 can include, or can optionally be combined with the subject matter of one or any combination of EMBODIMENTS 1-35, to optionally include the method increasing or improving detection of true biological variability.

EMBODIMENT 37 can include, or can optionally be combined with the subject matter of one or any combination of EMBODIMENTS 1-36, to optionally include the method maximizing detection of true biological variability.

EMBODIMENT 38 can include, or can optionally be combined with the subject matter of one or any combination of EMBODIMENTS 1-37, to optionally include the method reducing bias resulting from instrument variability.

EMBODIMENT 39 can include, or can optionally be combined with the subject matter of one or any combination of EMBODIMENTS 1-38, to optionally include the method minimizing bias resulting from instrument variability.

EMBODIMENT 40 can include, or can optionally be combined with the subject matter of one or any combination of EMBODIMENTS 1-39, to optionally include the method reducing bias resulting from sample handling variability.

EMBODIMENT 41 can include, or can optionally be combined with the subject matter of one or any combination of EMBODIMENTS 1-40, to optionally include the method minimizing bias resulting from sample handling variability.

EMBODIMENT 42 can include, or can optionally be combined with the subject matter of one or any combination of EMBODIMENTS 1-41, to optionally include the method reducing bias resulting from loading amount variability.

EMBODIMENT 43 can include, or can optionally be combined with the subject matter of one or any combination of EMBODIMENTS 1-40, to optionally include the method minimizing bias resulting from loading amount variability.

EMBODIMENT 44 can include, or can optionally be combined with the subject matter of one or any combination of EMBODIMENTS 1-43, to optionally include the method normalizing without overfitting.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:

loading a biological sample including analytes onto a high-performance liquid chromatography column;

separating one or more of the analytes in the high-performance liquid chromatography column to provide one or more separated analytes;

ionizing the one or more separated analytes with electrospray ionization to provide ions;

subjecting the ions to tandem mass spectrometry to produce first and second data distributions indicative of abundance of one or more of the analytes within the biological sample;

globally normalizing, with a computer, the first and second data distributions by normalizing proximal compositional proportionality of the abundance of the one or more analytes using a proximity-based intensity normalization, wherein the proximity-based intensity normalization comprises using the following formula:

$$\frac{i_{jx}}{\sum_{j=1}^{n_x} i_{jx}} \bigg/ \frac{i_{jy}}{\sum_{j=1}^{n_y} i_{jy}}$$

wherein:

$i_{jx}$ is the intensity of ion j in the first distribution x, $i_{jy}$ is the intensity of ion j in the second distribution y, $n_x$ is the number of surrogate ions in distribution x, and $n_y$ is the number of surrogate ions in distribution y; and determining, based on the globally normalized first and second data distributions, whether variance of the data points indicating abundance of one or more of the analytes between the first and second data distributions is due to biological variability or due to extraneous variability between the first and second data distributions comprising complex variability resulting from one or more transient stochastic events occurring during one or more of the loading step, the separating step, the ionizing step, and the subjecting step, wherein the determining step comprises the computer using the proximity-based intensity normalization to mitigate bias resulting from the complex variability.

2. The method of claim 1, wherein the method improves the ability to produce a consistent result in at least one of: a repeated measurement of a same biological sample using a same system and operator; and a repeated experiment where analytical technique remains the same.

3. The method of claim 1, wherein the analytes comprises one or more polymers, the method further comprising analyzing the biological sample for quantitation of the one or more polymers.

4. The method of claim 3, wherein the one or more polymers comprises at least one of deoxyribonucleic acid (DNA), ribonucleic acid (RNA), peptide nucleic acid (PNA), one or more proteins, one or more peptides, one or more carbohydrates, and modified forms thereof.

5. The method of claim 1, wherein the analytes comprises a pharmaceutical compound, the method further comprising analyzing the biological sample for quantitation of the pharmaceutical compound.

6. The method of claim 1, wherein the biological sample comprises at least one of blood and urine.

7. The method of claim 1, further comprising computing, with the computer, a proportional ratio of the analytes between the first and second data distributions.

8. The method of claim 1, further comprising reducing, with the computer, at least one of: a median standard deviation coefficient of variance quality metric and a median standard deviation pooled estimate of variance quality metric.

9. The method of claim 1, wherein the extraneous variability between the first and second data distributions further comprises systemic bias; and wherein the determining step comprises the computer using the proximity-based intensity normalization to mitigate bias resulting from the complex variability and from the systemic bias.

10. The method of claim 9, wherein the systemic bias comprises one or more of bias resulting from instrument variability, bias resulting from sample preparation variability, bias resulting from sample handling variability, and bias resulting from loading amount variability, and wherein the determining step comprises the computer using the proximity-based intensity normalization to mitigate one or more of the bias resulting from instrument variability, the bias resulting from sample preparation variability, the bias resulting from sample handling variability, and the bias resulting from loading amount variability.

11. The method of claim 10, wherein the instrument variability comprises variability due to a change in hardware or environment during one or more of the loading step, the separating step, and the ionizing step, and wherein the determining step comprises the computer using the proximity-based intensity normalization to mitigate bias resulting from the variability due to the change in hardware or environment during one or more of the loading step, the separation step, the ionizing step, and the subjecting step.

12. The method claim 1, further comprising, with the computer, increasing detection of true biological variability.

13. The method of claim 1, wherein the method normalizes without overfitting.

14. The method of claim 1, wherein the complex variability comprises one or both of mobile phase composition fluctuation during the ionizing step and flow rate fluctuation during the ionizing step, and wherein the determining step comprises the computer using the proximity-based intensity normalization to mitigate one or both of bias resulting from the mobile phase composition fluctuation during the ionizing step and bias resulting from the flow rate fluctuation during the ionizing step.

* * * * *